US005563148A

United States Patent [19]

Cohen et al.

[11] Patent Number: 5,563,148

[45] Date of Patent: Oct. 8, 1996

[54] SPECIFIC 5-HT3 ANTAGONISTS

[75] Inventors: Marlene L. Cohen; William B. Lacefield, both of Indianapolis; David W. Robertson, Greenwood, all of Ind.

[73] Assignee: Eli Lilly and Company, Indianapolis, Ind.

[21] Appl. No.: 427,773

[22] Filed: Apr. 25, 1995

Related U.S. Application Data

[62] Division of Ser. No. 263,858, Jun. 22, 1994, Pat. No. 5,442,078, which is a division of Ser. No. 53,061, Apr. 26, 1993, Pat. No. 5,364,863, which is a division of Ser. No. 730,718, Jul. 16, 1991, abandoned, which is a division of Ser. No. 598,297, Oct. 16, 1990, abandoned, which is a division of Ser. No. 471,754, Jan. 24, 1990, Pat. No. 4,997,956, which is a division of Ser. No. 366,343, Jun. 14, 1989, Pat. No. 4,921,982, which is a continuation of Ser. No. 222,466, Jul. 21, 1988, abandoned, which is a continuation-in-part of Ser. No. 94,360, Sep. 8, 1987, abandoned.

[51] Int. Cl.$^6$ ........................ A61K 31/46; A61K 31/435; C07D 451/06; C07D 453/02

[52] U.S. Cl. ........................ 514/299; 514/221; 514/224.2; 514/230.5; 514/304; 514/305; 540/582; 544/47; 544/105; 546/112; 546/126; 546/134; 546/183

[58] Field of Search .................................... 546/112, 134, 546/126, 183; 540/582; 544/47, 105; 514/221, 224.2, 230.5, 299, 304, 305

[56] References Cited

U.S. PATENT DOCUMENTS

| | | | |
|---|---|---|---|
| 3,860,619 | 1/1975 | Christensen et al. | 549/471 |
| 4,329,459 | 5/1982 | McCall | 544/264 |
| 4,486,441 | 12/1984 | Fozard et al. | 424/265 |
| 4,888,353 | 12/1989 | Lednuer et al. | 514/422 |

FOREIGN PATENT DOCUMENTS

| | | | |
|---|---|---|---|
| 95262 | 11/1983 | European Pat. Off. | C07D 451/04 |
| 0147044 | 7/1985 | European Pat. Off. | C07D 307/79 |
| 128265 | 10/1985 | European Pat. Off. | C07D 451/04 |
| 0189002 | 12/1985 | European Pat. Off. | A61K 31/445 |
| 200555 | 11/1986 | European Pat. Off. | C07D 451/12 |
| 223385 | 5/1987 | European Pat. Off. | C07D 451/12 |
| 0234872 | 9/1987 | European Pat. Off. | C07D 307/79 |
| 2042522 | 9/1980 | United Kingdom | C07D 451/04 |
| 2125398 | 3/1984 | United Kingdom | C07D 451/12 |
| 2152049 | 7/1985 | United Kingdom | C07D 451/06 |
| 84/03281 | 8/1984 | WIPO | C07D 451/04 |

OTHER PUBLICATIONS

Gazz, Chim. Ital., 3(9–10), 383 (1981).

Occelli et al., Chem. Abst., vol. 96, 142391 (1982).

Rorer, Chem. Abst., vol. 99, 53792 (1983).

Christensen et al., Chem. Abst. (II), vol. 78, 147774 (1973).

Serban et al., Chem. Abst., vol. 84, 59722 (1976).

*Primary Examiner*—Bernard Dentz
*Attorney, Agent, or Firm*—Robert A. Conrad

[57] ABSTRACT

This invention provides bicyclic carboxylic esters and amides, their pharmaceutical formulations, and a method for their use in treating migraine, emesis, gastrointestinal disorders, schizophrenia, or anxiety in mammals.

28 Claims, No Drawings

SPECIFIC 5-HT3 ANTAGONISTS

CROSS-REFERENCE

This application is a division of Ser. No. 08/263,858 filed Jun. 22, 1994 now U.S. Pat. No. 5,442,078, which is a division of Ser. No. 08/053,061, filed Apr. 26, 1993, now U.S. Pat. No. 5,364,863, which is a division of Ser. No. 07/730,718, filed Jul. 16, 1991, now abandoned, which is a division of Ser. No. 07/598,297, filed Oct. 16, 1990, now abandoned, which is a division of Ser. No. 07/471,754, filed Jan. 24, 1990, now U.S. Pat. No. 4,997,956, which is a division of Ser. No. 07/366,343, filed Jun. 14, 1989, now U.S. Pat. No. 4,921,982, which is a continuation of Ser. No. 07/222,466, filed Jul. 21, 1988, now abandoned, which is a continuation-in-part of Ser. No. 07/094,360, filed Sep. 8, 1987, now abandoned.

BACKGROUND OF THE INVENTION

A variety of agents are presently under development as potential treatments for migraine headaches. For example, MDL-72222 (tropine 3,5-dichlorobenzoate) is reported to block the M-receptors for 5-hydroxytryptamine (5-HT), now referred to as $5\text{-HT}_3$ receptors, thereby providing an anti-migraine effect—see Bradley, et al., *Neuropharmacology,* 25 (6), 563 (1986). Other $5\text{-HT}_3$ antagonists reported in the literature include Beecham compound 112-574, included in EPO Patent Application Publication 158,265, and Merrell-Toraude compound 105-834, (U.S. Pat. No. 4,486,441). All of these compounds are tropine or tropine-like esters or amides of a substituted benzoic acid.

Indole and related bicyclic derivatives are also reported to be anti-migraine agents. See, e.g., GB 2,125,398. Other bicyclic derivatives are reported in WO 84/03281 to have dopamine antagonist activity and to be useful for lowering blood pressure and treating emesis.

This invention provides potent specific $5\text{-HT}_3$ antagonists useful for treating migraine and emesis. The compounds are potent, orally active, and provide a long duration of effect.

SUMMARY OF THE INVENTION

This invention provides compounds of the Formula I

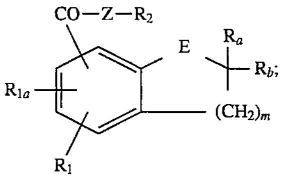

I and pharmaceutically acceptable acid addition salts thereof: wherein $R_a$ and $R_b$ are independently hydrogen, methyl, or ethyl, or when taken together with the carbon atom to which they are attached form a $C_3$–$C_6$ cycloalkyl ring, provided that $R_a$ and $R_b$ may not both be hydrogen at the same time;

E is O, NH, or S;

$R_1$ and $R_{1_a}$ are independently hydrogen, methyl, halo, $C_1$–$C_3$ alkoxy, ($C_1$–$C_3$ alkyl)-S(O)$_t$-, trifluoromethyl, amino, hydroxy, $(CH_3)_2NSO_2$-, or ($C_1$–$C_4$ alkyl-)CONH-;

m is 1 or 2;

t is 0, 1, or 2;

Z is O or NH; and $R_2$ is quinuclidine, quinuclidine N-oxide, 1-azabicyclo [3.3.1]non-4-yl,

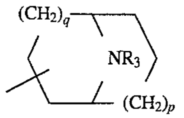

$R_2$ a

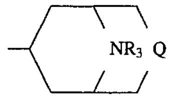

or $R_2$ b

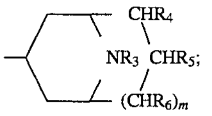

$R_2$ c wherein $R_3$ is $C_1$–$C_3$ alkyl, p and q are independently 0–2; Q is O or s; n is 0 or 1; one of $R_4$ and $R_5$ when n is 0 is $C_1$–$C_4$ alkoxy, $C_1$–$C_4$ alkoxycarbonyl, hydroxy, or $C_1$–$C_4$ alkyl optionally substituted by hydroxy, $C_1$–$C_4$ alkoxy, or $C_1$–$C_4$ acyloxy and the other of $R_4$ and $R_5$ is hydrogen or $C_1$–$C_4$ alkyl; one of $R_4$, $R_5$, and $R_6$ when n is 1 is $C_1$–$C_4$ alkyl and the other two of $R_4$, $R_5$, and $R_6$ are independently hydrogen or $C_1$–$C_4$ alkyl.

Further provided by this invention is a method of treating migraine, emesis, gastrointestinal disorders, schizeophrenia, or anxiety in a mammal which comprises administering to said mammal an effective amount of a compound of Formula I.

Also provided by this invention is a pharmaceutical composition comprising a compound of this invention in combination with a pharmaceutically acceptable carrier, diluent or excipient.

This invention also provides aryl carboxylic acid compounds of the Formula IIa

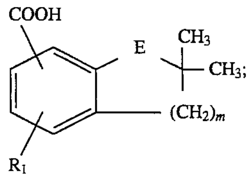

IIa wherein m is 1 or 2;

E is O, NH or S, and $R_1$ is hydrogen, methyl, halo, trifluoromethyl, ($C_1$–$C_3$ alkyl)-S(O)$_t$-, or methoxy.

These compounds are useful as intermediates in preparing some of the pharmaceutically useful compounds of this invention.

DETAILED DESCRIPTION AND PREFERRED EMBODIMENTS

Many of the functionalities and substituents part of $R_2$ are similarly provided in WO 84/03281 and the definitions of the substituents as presently employed, to the extent consistent in scope with that found in the reference, are considered to be identical as reported therein.

The term "$C_3$–$C_6$ cycloalkyl ring" refers to cyclopropyl, cyclobutyl, cyclopentyl, and cyclohexyl. The term "$C_1$–$C_3$ alkoxy" refers to methoxy, ethoxy, propoxy, or isopropoxy. The term "$C_1$–$C_4$ alkyl" refers to methyl, ethyl, propyl, isopropyl, butyl, isobutyl, sec-butyl, and tert-butyl and includes within its definition the term "$C_1$–$C_3$ alkyl". The term "halo" includes fluoro, chloro, and bromo.

The preferred compounds of this invention are those of Formula Ia

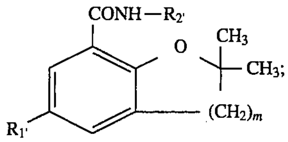

Ia wherein m is 1 or 2, $R_{1'}$ is hydrogen, methyl, fluoro, bromo, or especially chloro, $R_{2'}$ is a tropane ring, i.e., an endo (or 3α) 8-methyl-8-azabicyclo[3.2.1]oct- 3-yl group, quinuclidine, i.e., 1-azabicyclo[2.2.2]oct- 3-yl, or endo-9-methyl-9-azabicyclo[3.3.1]non-3-yl.

The pharmaceutically acceptable acid addition salts of this invention are addition salts with suitable acids, such as those with inorganic acids, for example hydrochloric, hydrobromic, nitric, sulfuric, or phosphoric acids, or with organic acids, such as organic carboxylic acids, for example glycolic, maleic, hydroxymaleic, malic, tartaric, citric, lactic, and the like, or organic sulfonic acids, for example, methanesulfonic, ethanesulfonic, p-toluenesulfonic, or naphthalene-2-sulfonic acids. In addition to the pharmaceutically acceptable salts listed above, other acid addition salts, such as those obtained with picric or oxalic acid, may serve as intermediates useful in the purification of the compounds of this invention or in the preparation of other, for example, pharmaceutically acceptable, acid addition salts. In addition, these salts may also be useful for identification or characterization of the compounds of this invention.

Also contemplated within the scope of the present invention are hydrates of the compounds or their various salts, or other solyates, such as that formed with ethanol or other non-toxic solvents.

It is appreciated that when $R_a$ and $R_b$ are different, or when $R_4$, $R_5$ or $R_6$ are other than hydrogen, various stereoisomers are possible. Similarly, the $R_2$ ring may be in the α- or β-position. This invention includes all individual isomers and the various mixtures thereof.

The compounds of the present invention are prepared according to Scheme 1.

Scheme 1

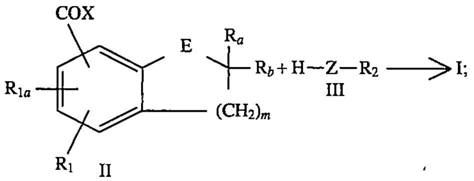

where X is OH or a carboxylic acid activating group such as chloro, bromo, $C_1$–$C_4$ acyloxy (a mixed anhydride), and the like.

The reaction between II, where X is an activating group, and III is well known in the art as demonstrated in U.S. Pat. No. 4,486,441, EPO Patent Application Publication 158, 265, and WO 84/03281, which references are expressly incorporated into this application. Preferably, the carboxylic acid (II, X is OH) is converted to the corresponding acid chloride (II, X is —Cl) upon treatment with an excess of a reagent such as thionyl chloride. When thionyl chloride is employed, it is preferably used both as the reagent and as solvent. The reaction mixture is usually heated at reflux for 1–3 hours to bring the reaction to completion. The resulting acid chloride is then treated with the appropriate amine or alcohol III. Usually, a 1- to 2-fold molar excess of III is employed. In addition, an inert solvent, such as toluene, is preferably used as a more convenient means of allowing the reaction to proceed. When a solvent is used, the mixture is preferably heated at reflux and under an inert atmosphere to drive the reaction to completion. Other variations of this process, including different concentrations, molar proportions, solvents, etc. will be apparent to those skilled in the art. For example, one may employ peptide coupling reagents, such as 1,1'-carbonyldiimidazole, with the carboxylic acid of Formula II, followed by introduction of III to the reaction mixture.

The general chemistry for preparing intermediates II and III is well known in the art. In particular, many of the amines of Formula III are employed in WO 84/03281. These and other necessary intermediates are either commercially available, known in the literature, or can be prepared by methods known in the art.

In addition, the preparation of intermediates II is similar to that taught in WO 84/03281. The preferred method of preparing the 2,2-dimethyl 6.5 bicyclic compounds is provided in Scheme 2 which follows.

Scheme 2

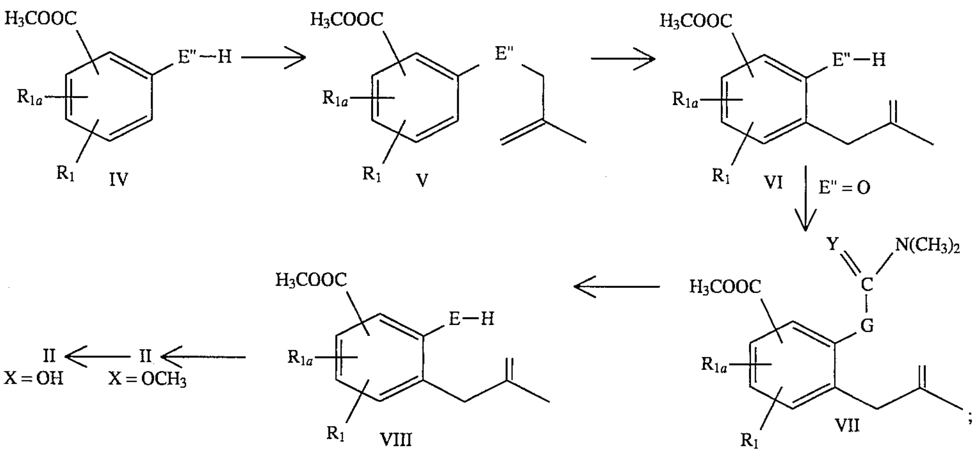

wherein one of G and Y is O and the other is S, and E" is O or NH.

Accordingly to Scheme II, the phenol or aniline of Formula IV is alkylated with 2-methyl-2-propenyl bromide or chloride to provide intermediate V. This transformation is usually accomplished by heating near equimolar amounts of the two reagents together with an acid scavenger, such as potassium carbonate, and an inert solvent, such as acetone, at temperatures from about ambient temperature up to the reflux temperature of the reaction mixture. The alkylated intermediate V is then subjected to a Claisen rearrangement to provide the phenol or aniline of Formula VI. This rearrangement is accomplished by heating V to temperatures of about 150°–200° C., preferably in a non-reactive solvent such as 1-methyl-2-pyrrolidinone.

In order to prepare the dihydrobenzothiophenes of this invention, intermediate VI (E"=O) is treated with dimethylthiocarbamoyl chloride to provide VII (G=O; Y=S). This transformation involves a standard acylating procedure which commonly uses a strong base, such as sodium hydride, and a non-reactive solvent, such as dimethylformamide. When heated neat at 220°–230° C. for approximately 10 minutes, this thionic acid derivative rearranges to provide the corresponding thiolic intermediate VII (G=S; Y=O) which, upon treatment with base, such as sodium hydroxide, provides the free thiol derivative VIII (E=S). This hydrolysis potentially also hydrolyzes the ester which can be reesterified by conventional means. Alternatively, the acid analogue of VIII (E=S) may be used for the subsequent cyclization.

The conversion of VIII to the bicyclic ester II ($X=OCH_3$) can be accomplished by heating with 90% formic acid at reflux temperatures for 2–3 hours. As mentioned above, in the special case where E is S, the transformation can be accomplished either on the carboxylic acid or ester upon treatment with an alcohol, such as methanol or ethanol, which is saturated with hydrogen chloride gas. This transformation not only results in ring closure, but also reesterifies the free acid. This latter transformation is most efficient when the reaction mixture is allowed to reflux for 16–20 hours.

Alternatively, the intermediate of Formula VIII can be treated with hydrogen bromide in a non-reactive solvent such as chloroform to prepare the corresponding alkyl bromide intermediate which can be isolated or used in situ to prepare II (X=OH) upon treatment with alcoholic sodium or potassium hydroxide. See, e.g., U.S. Pat. No. 3,860,619.

The esters of Formula II are transformed into the carboxylic acid intermediates (II, X=OH) by standard methods of hydrolysis. Typically, the treatment of the ester with an aqueous solution of an inorganic base, such as potassium or sodium hydroxide, is sufficient to convert the ester to the free acid when allowed to reflux for 2–3 hours. Other methods of effecting this transformation are readily apparent to those skilled in the art.

The related 6.6 bicyclic systems and alkyl variations of $R_a$ and $R_b$ can be prepared by methods analogous to that taught in Scheme 2 above employing the appropriate starting materials, by other means such as are described below, or are provided in the art, such as WO 84/03281.

Other transformations and intraconversions of the compounds of this invention can be accomplished. For example, amino groups may be introduced onto the benzene portion of the bicyclic moiety either as intermediates such as Formulas II and IIa or final products of Formula I. Typically, one or two nitro groups are introduced by direct nitration of the intermediate or final product employing a mixture of nitric and sulfuric acids. The transformation of a nitro group into an amine is readily accomplished by hydrogenation, for example, in the presence of a 5% palladium-on-carbon catalyst in a non-reactive solvent such as ethyl acetate. One or two nitro groups may be introduced either at the same time or sequentially, i.e., a second nitro group may be introduced after the first has been transformed into the amine.

Halo groups may also be directly introduced at the intermediate or final product stage. Typically, this can be accomplished by treating the intermediate or final product with a halogenating reagent such as iodobenzene dichloride in pyridine or some like halogenating reagent. In like manner, a halogen group can be removed from an intermediate or final product to form the comparable hydrogen-substituted derivative. This is best accomplished by subjecting the intermediate or final product to hydrogenation conditions.

Other transformations and interconversions will be apparent to one skilled in the art. For example, hydroxy-substituted compounds can be prepared from the corresponding alkoxy, particularly the methoxy, substituted intermediates or final products by dealkylating with an appropriate reagent. A preferred such reagent is the use of molten pyridine hydrochloride which is very effective for effecting this transformation. In like manner, an N,N-dimethylsulfonamido group can be introduced onto the benzene ring of the bicycle by treating the precursor intermediate or final product with chlorosulfonic acid in an inert solvent such as ethylene dichloride at low temperature followed by treatment with dimethylamine. As will be appreciated by the skilled artisan, the particular sequence for effecting such transformations can be determined depending upon the particular substituent and position of the substituent desired.

One additional transformation involves the use of a blocking group on the $R_2$ portion of the molecule which can be removed and the resulting secondary amino group realkylated to provide a compound of the present invention. For example, those $R_{2_a}$, $R_{2_b}$, and $R_{2_c}$ analogues wherein $R_3$ is benzyl can be introduced into the final product to provide the corresponding N-benzyl cognate. The N-benzyl group may be removed by standard means, such as by subjecting the intermediate to hydrogenation conditions. The resulting secondary amine can then be alkylated with the appropriate $C_1$–$C_4$ alkyl halide in an inert solvent such as tetrahydrofuran or isopropyl alcohol, optionally in the presence of an acid scavenger such as sodium carbonate. Other such blocking groups and means for deblocking will be apparent to those skilled in this art.

The thio derivatives and intermediates of this invention (t is 0) may be transformed into the corresponding sulfoxide (t is 1) compounds upon treatment with a mild oxidizing agent, such as hydrogen peroxide in methanol, meta-chloroperbenzoic acid (MCPBA) in methylene chloride at 0° C., or an alkali metal periodate in aqueous alcohol. The corresponding sulfones (t is 2) are prepared from the thio or sulfoxide compounds on treatment with a strong oxidizing agent such as hydrogen peroxide in acetic acid or m-chloroperbenzoic acid in methylene chloride at 20°–30° C.

Intermediates IV, and other reagents necessary for preparing the intermediates and compounds of this invention, are commercially available, are known in the literature, or can be prepared by known methods. In addition, those skilled in the art will recognize that variations on the methods for preparing the claimed intermediates and compounds as described above may be performed without detracting from the synthesis of these compounds. For example, other esters may be employed, as may protecting groups, precursors, the direct introduction of the carboxylic acid group onto the phenyl ring of the bicycle (Kolbe-Schmitt reaction) etc. Moreover, certain $R_1$ substituents may be introduced directly onto the phenyl ring. For example, a chloro group can be introduced by treating with iodobenzene, chlorine, and pyridine (See Murakami et al., *Chem. Pharm. Bull.* 19, 1696 (1971)) or N-chlorosuccinimide in dimethylformamide (U.S. Pat. No. 4,623,657).

The spirocycloalkyl compounds of this invention can be prepared in a number of ways, such as that provided in Scheme 3:

Scheme 3

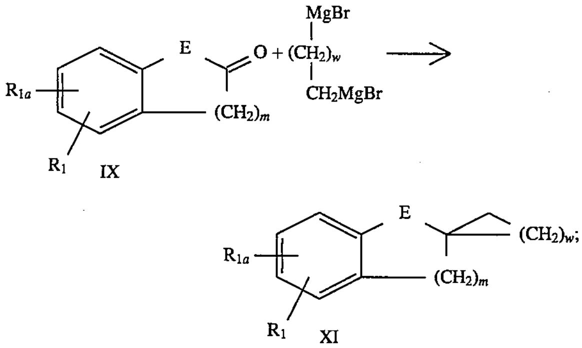

IX

XI where w is 1–4. This procedure is generally described in U.S. Pat. No. 4,329,459 which is incorporated herein by reference. The reaction is a double Grignard synthesis and introduces the spiro ring onto the bicyclic nucleus. The intermediate XI can then be carboxylated as described earlier.

In the special case of w=1 (the spirocyclopropyl compounds), the ketone of formula IX can be transformed into the corresponding exomethylene compound by any of a variety of procedures, such as the titanium-aluminum complex method of Pine, et al., *J.A.C.S.*, 102 (9), 3270 (1980). This exomethylene derivative can then be converted into the spirocyclopropyl compound by treatment with diiodomethane and zinc-copper by the procedure of Simmons and Smith, *J.A.C.S.*, 81, 4256 (1959). See also Organic Reactions, 20, Chapter 1, page 109.

The tricyclic compounds of formula XI can also be prepared according to U.S. Pat. No. 4,623,657, or obvious variations thereof. An illustrative example employing the chemistry of this reference is provided in Scheme 4.

Scheme 4

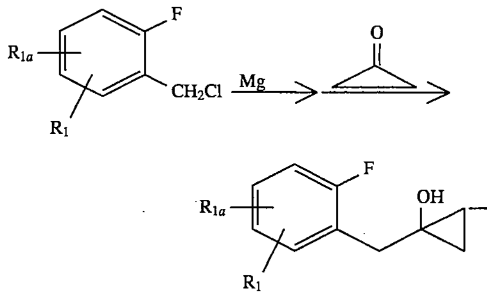

XI.
(w = m = 1)

The following examples further illustrate the preparation of the intermediates and compounds of this invention. The examples are illustrative only and are not intended to limit the scope of the invention in any way. Where structures were confirmed by infrared, proton nuclear magnetic resonance, or mass spectral analysis, the compound is so designated by "IR", "NMR", or "MS", respectively.

EXAMPLE 1

2,2-dimethyl-2,3-dihydrobenzothiophene-7-carboxylic acid

A. Preparation of 2-(2-methyl-2-propenyloxy)benzoic acid, methyl ester

A mixture of 152 g of methyl salicylate, 99 g of 3-chloro-2-methylpropene, 151.8 g of potassium carbonate, and 500 ml of acetone was heated at reflux overnight. After cooling, the mixture was extracted with diethyl ether and ethyl acetate. The organic extracts were combined, washed twice with a 10% sodium chloride solution and water, dried over sodium sulfate, and concentrated in vacuo. The resulting liquid was vacuumed distilled. The fraction collected at 120°–121° C. and 1.5 torr provided 76.2 g of the desired subtitle intermediate. NMR, MS.

Analysis for $C_{12}H_{14}O_3$: Calc.: C, 69.89; H, 6.84; Found: C, 70.02; H, 6.93.

B. Preparation of 2-hydroxy-3-(2-methyl-2-propenyl)benzoic acid, methyl ester

A solution of 76.2 g of the intermediate of Example 1A above was heated at reflux for 6 hours in 150 ml of 1-methyl-2-pyrrolidinone. The mixture was then vacuum distilled and the fraction collected at 104°–109° C. and 1.2 torr provided 60.6 g of the desired subtitle intermediate. MS.

Analysis for $C_{12}H_{14}O_3$: Calc.: C, 69.89; H, 6.84; Found: C, 69.87; H, 6.89.

C. Preparation of 2-[dimethylamino(thioxomethyl)oxy]-3-(2-methyl-2-propenyl)benzoic acid, methyl ester To 1 liter of dry dimethylformamide were added 16 g of 60% sodium hydride in oil. After stirring under a nitrogen atmosphere, 81.7 g of 2-hydroxy-3-(2-methylpropenyl)benzoic acid, methyl ester, as a solution in dimethylformamide, were added in dropwise fashion. After stirring at room temperature, a solution 49.6 g of dimethylthiocarbamoyl chloride in dimethylformamide was added over a one hour period. The reaction mixture was stirred at room temperature overnight, then poured onto ice and extracted with diethyl ether and ethyl acetate. The combined organic extracts were washed successively with a 10% sodium hydroxide solution and water, dried over sodium sulfate, and concentrated in vacuo. The residue was vacuum distilled, and the fraction distilling at 162°–168° C. and 0.6 torr provided 69.9 g of the desired subtitle intermediate. NMR, MS.

Analysis for $C_{15}H_{19}NO_3S$: Calc.: C, 61.41; H, 6.53; N, 4.77; Found: C, 64.87; H, 7.45; N, 4.37.

D. Preparation of 2-[(dimethylamino)carbonylthio]-3-(2-methyl-2-propenyl)benzoic acid, methyl ester The intermediate from Example 1C above (69.5 g) was heated to 220°–230° C. for 10–15 minutes. After cooling, the residue was vacuum distilled. The fraction collected at 153°–155° C. and 0.1 torr and the remaining distillation residue were combined and purified by high pressure liquid chromatography over silica gel eluting with 20% ethyl acetate in toluene. The appropriate fractions were combined and concentrated in vacuo to provide 41.8 g of the desired subtitle intermediate. MS, IR, NMR.

Analysis for $C_{15}H_{19}NO_3S$: Calc.: C, 61.41; H, 6.53; N, 4.77; Found: C, 61.40; H, 6.30; N, 5.05.

E. Preparation of 2-mercapto-3-(2-methyl-2-propenyl)benzoic acid

The 41.8 g of intermediate from Example 1D above were heated at reflux for 18 hours with 175 ml of methanol and 12 g of sodium hydroxide. The reaction mixture was poured into ice water and extracted with ethyl acetate. The aqueous layer was made acidic with hydrochloric acid and extracted again with ethyl acetate. The organic layer was washed with water, dried over sodium sulfate, and concentrated in vacuo providing 28.8 g of desired subtitle intermediate, m.p. 89°–92° C. NMR, MS.

Analysis for $C_{11}H_{12}O_2S$: Calc.: C, 63.43; H, 5.81; Found: C, 63.69; H, 5.89.

F. Preparation of 2,2-dimethyl-2,3-dihydrobenzothiophene-7-carboxylic acid, methyl ester A mixture of 23.8 g of the intermediate from Example 1E above and 1 liter of methanol was saturated with hydrogen chloride gas and then refluxed overnight. The solution was concentrated in vacuo, added to water, and extracted with ethyl acetate. The organic layer was washed with water, dried over sodium sulfate, and concentrated in vacuo, providing 24.1 g of the desired subtitle intermediate as an oil. MS.

Analysis for $C_{12}H_{14}O_2S$: Calc.: C, 64.83; H, 6.35; Found: C, 64.56; H, 6.33.

G. Preparation of 2,2-dimethyl-2,3-dihydrobenzothiophene-7-carboxylic acid

The 24.1 g of ester product from Example 1F above were heated at reflux with 50 g of sodium hydroxide and 200 ml of water for 2–3 hours. After cooling, the mixture was extracted with diethyl ether and ethyl acetate. The aqueous layer was acidified with hydrochloric acid and again extracted with ethyl acetate and diethyl ether. These latter organic extracts were combined and washed with water, dried over sodium sulfate, and concentrated in vacuo. Crystallization of the resulting solid from ethyl acetate/hexane provided 8.8 g of the desired title intermediate, m.p. 179°–182° C. NMR, MS.

Analysis for $C_{11}H_{12}O_2S$: Calc.: C, 63.43; H, 5.81; Found: C, 63.18; H, 6.10.

EXAMPLES 2–14

The following compounds were prepared from the corresponding methyl esters according to the procedure of Example 1G. The general preparation of the ester intermediates followed that of Examples 1A, 1B, and a variation of 1F wherein 90% formic acid was employed in place of the hydrogen chloride/methanol combination. 2-Monomethyl derivatives were prepared according to the procedure of Example 1A using allyl bromide in place of 3-chloro-2-methylpropene followed by subsequent transformations in the same way. Yields are expressed as the molar percent yield from the ester except as indicated.

2. 2,2-Dimethyl-2,3-dihydrobenzofuran-7-carboxylic acid, 82% yield (from the 2-methyl-2-propenyloxy intermediate), m.p. 135°–137° C. NMR, MS.

Analysis for $C_{11}H_{12}O_3$: Calc.: C, 68.74; H, 6.29; Found: C, 69.04; H, 6.47.

3. 2,2-Dimethyl-4-chloro-2,3-dihydrobenzofuran- 7-carboxylic acid, 87% yield, m.p. 195°–197° C.

Analysis for $C_{11}H_{11}ClO_3$: Calc.: C, 58.29; H, 4.89; Found: C, 58.55; H, 4.76.

4. 2,2-Dimethyl-5-chloro-2,3-dihydrobenzofuran- 7-carboxylic acid, 71% yield (from the 2-methyl-2-propenylphenol intermediate), m.p. 158.5°–160° C. NFFR, MS.

Analysis for $C_{11}H_{11}ClO_3$: Calc.: C, 58.29; H, 4.89; Found: C, 58.08; H, 4.65.

5. 2,2-Dimethyl-2,3-dihydrobenzofuran-5-carboxylic acid, 61% yield, m.p. 174°–176° C. NMR, MS.

Analysis for $C_{11}H_{12}O_3$: Calc.: C, 68.74; H, 6.29; Found: C, 68.51; H, 6.34.

6. 2,2,5-Trimethyl-2,3-dihydrobenzofuran-7-carboxylic acid, 82% yield, m.p. 170°–172° C. NMR, MS.

Analysis for $C_{12}H_{14}O_3$: Calc.: C, 69.89; H, 6.84; Found: C, 70.19; H, 6.89.

7. 2,2-Dimethyl-2,3-dihydrobenzofuran-4-carboxylic acid, 66% yield (from the 2-methyl-2-propenylphenol intermediate), m.p. 174°–176° C. MS, Analysis for $C_{11}H_{12}O_3$: Calc.: C, 68.74; H, 6.29; Found: C, 68.89; H, 6.25.

8. 2,2-Dimethyl-2,3-dihydrobenzofuran-6-carboxylic acid, 80% yield, m.p. 138°–141° C. NMR, MS.

Analysis for $C_{11}H_{12}O_3$: Calc.: C, 68.74; H, 6.29; Found: C, 68.50; H, 6.08.

9. 2 -Methyl-5-methoxy-2,3-dihydrobenzofuran-7-carboxylic acid, 100% yield (from the 2-allylphenol intermediate via the bromo intermediate), m.p. 120°–121° C.

Analaysis for $C_{11}H_{12}O_4$: Calc.: C, 63.45; H, 5.81; Found: C, 63.22; H, 5.87.

10. 2,2-Dimethyl-7-chloro-2,3-dihydrobenzofuran- 5-carboxylic acid, 72% yield, m.p. 189°–190° C.

Analysis for $C_{11}H_{11}ClO_3$: Calc.: C, 58.29; H, 4.89; Found: C, 58.40; H, 4.93.

11. 2-Methyl-5-fluoro-2,3-dihydrobenzofuran- 7-carboxylic acid, 72% yield, m.p. 129.5°–131.5° C.

Analysis for $C_{10}H_9FO_3$: Calc.: C, 61.23; H, 4.62; Found: C, 61.41; H, 4.78.

12. 2-Methyl-2,3-dihydrobenzofuran-7-carboxylic acid, 88% yield (from the 2-(2-bromopropyl)phenol intermediate), m.p. 125°–127° C.

Analysis for $C_{10}H_{10}O_3$: Calc.: C, 67.03; H, 6.19; Found: C, 67.23; H, 5.99.

13. 2-Methyl-5-chloro-2,3-dihydrobenzofuran- 7-carboxylic acid, 21% yield (from the 2-(2-bromopropyl)phenol intermediate), m.p. 184°–188° C.

Analysis for $C_{10}H_9ClO_3$: Calc.: C, 56.49; H, 4.27; Found: C, 56,56; H, 4.38.

14. 2,2-Dimethyl-5-methoxy-2,3-dihydrobenzofuran-7-carboxylic acid, 68% yield, m.p. 140°–142° C.

Analysis for $C_{12}H_{14}O_4$: Calc.: C, 64.85; H, 6.35; Found: C, 64.99; H, 6.25.

EXAMPLE 15

2,2-Dimethylchroman-8-carboxylic acid

A. Preparation of 2-(3-methyl-3-hydroxybutyl)phenol

To a solution of 200 ml of 3M methyl magnesium chloride in tetrahydrofuran (THF) and 150 ml of THF was added a solution 44.4 g of dihydrocoumarin in THF over a 40 minute period. An additional 150 ml of THF were added and, after cooling the resulting exotherm, the mixture was stirred at room temperature overnight. The solution was cooled and treated with 50 ml of a saturated ammonium chloride solution and 100 ml of water. After stirring one hour, the mixture was added to ice water and extracted with diethyl ether. The organic layer was washed with water, dried over sodium sulfate, and concentrated in vacuo to provide 57.5 g of the desired subtitle intermediate, m.p. 113°–115° C.

B. Preparation of 2,2-dimethylchroman

The 57.5 g of phenol from Example 15A above were dissolved in 320 ml of acetic acid and 120 ml of 20% sulfuric acid and heated to reflux for 45 minutes. The solution was cooled, added to ice, and extracted with diethyl ether. The organic layer was washed with 200 ml of 10% sodium hydroxide and water, dried over sodium sulfate, and concentrated in vacuo. Vacuum distillation at 83°–85° C. and approximately 5 torr provided 36.3 g of the desired subtitle intermediate.

C. Preparation of 2,2-dimethylchroman-8-carboxylic acid

To a solution of 1.6M n-butyllithium in hexane and 150 ml of diethyl ether were added a solution of 27 g of 2,2-dimethylchroman in diethyl ether over a one hour period at room temperature. The solution was then heated at reflux 160 minutes, cooled, and poured into dry ice/diethyl ether. The mixture was allowed to come to room temperature, poured into ice water, and layers separated. The organic layer was washed with water, dried over sodium sulfate, and concentrated in vacuo to provide 21 g of solid. The aqueous layer was acidified and the resulting precipitate extracted into diethyl ether/ethyl acetate. The organic extract was washed with water, dried over sodium sulfate, and concentrated in vacuo to provide 9 g of solid. The two isolated solids were combined and chromatographed over silica gel eluting with 10% ethyl acetate in toluene. The appropriate fractions were combined and concentrated in vacuo to provide 9.8 g of the desired title intermediate, m.p. 90°–92° C.

Analysis for $C_{12}H_{14}O_3$: Calc.: C, 69.89; H, 6.84; Found: C, 69.84; H, 7.12.

EXAMPLE 16

Endo-2,3-dihydro-2,2-dimethyl-N-(8-methyl-8-azabicyclo[3.2.1]oct-3-yl)benzo[b]thiophene-7-carboxamide (Z)-2-butenedioate A mixture of 8.8 g of 2,2-dimethyl-2,3-dihydrobenzothiophene- 7-carboxylic acid and 119 g of thionyl chloride was heated at reflux for 3 hours. After the mixture was concentrated in vacuo and azeotroped with toluene, dry toluene was added and the solution cooled to 5° C. A solution of 7 g of tropamine in toluene was added in dropwise fashion and the reaction heated at reflux overnight. After cooling, the mixture was added to ice water, made basic, and extracted with diethyl ether/ethyl acetate. The organic layer was washed twice with 6N hydrochloric acid. The combined aqueous extracts were cooled, made basic with sodium hydroxide solution, and extracted with ethyl acetate. The ethyl acetate solution was washed twice with water, dried over sodium sulfate, and concentrated in vacuo providing 11.6 g of the title product free base as an oil. The maleate salt was then prepared and crystallized from ethanol/diethyl ether/ethyl acetate providing 11.5 g of the desired title product, 197°–199° C. NMR, MS.

Analysis for $C_{23}H_{30}N_2O_5S$: Calc.: C, 61.86; H, 6.77; N, 6.27; Found: C, 61.58; H, 6.84; N, 6.10.

EXAMPLES 17–42

The following products were prepared from the corresponding carboxylic acid via the acid chloride according to the procedure of Example 16 employing the appropriate amine or alcohol derivative of tropane.

17. Endo-2,3-dihydro-2,2-dimethyl-N-(8-methyl-8-azabicyclo[3.2.1]oct-3-yl)-7-benzofurancarboxamide (Z)-2-butenedioate, 61% yield, m.p. 163°–164° C.

Analysis for $C_{23}H_{30}N_2O_6$: Calc.: C, 64.17; H, 7.02; N, 6.51; Found: C, 64.20; H, 7.25; N, 6.29.

18. Endo-4-chloro-2,3-dihydro-2,2-dimethyl-N-( 8-methyl-8-azabicyclo[3.2.1]oct-3-yl)-7-benzofurancarboxamide (Z)-2-butenedioate, 100% yield, m.p. 198°–200° C.

Analysis for $C_{23}H_{29}ClN_2O_6$: Calc.: C, 59.42; H, 6.29; N, 6.03; Found: C, 59.58; H, 6.38; N, 6.23.

19. Endo-5-chloro-2,3-dihydro-2,2-dimethyl-N-( 8-methyl-8-azabicyclo[3.2.1.]oct-3-yl)-7-benzofurancarboxamide (Z)-2-butenedioate, 74% yield, m.p. 184°–186° C.

Analysis for $C_{23}H_{29}ClN2O_6$: Calc.: C, 59.42; H, 6.29; N, 6.03; Found: C, 59.23; H, 6.18; N, 6.14.

20. Endo-2,3-dihydro-2,2-dimethyl-N-(8-methyl-8-azabicyclo[3.2.1]oct-3-yl)-5-benzofurancarboxamide (Z)-2-butenedioate, 83% yield, m.p. 193°–195° C.

Analysis for $C_{23}H_{30}N_2O_6$: Calc.: C, 64.17; H, 7.02; N, 6.51; Found: C, 63.89; H, 6.85; N, 6.42.

21. Endo-2,3-dihydro-2,2,5-trimethyl-N-(8-methyl-8-azabicyclo[3.2.1]oct-3-yl)-7-benzofurancarboxamide (Z)-2-butenedioate, 65% yield, m.p. 173°–174° C.

Analysis for $C_{24}H_{32}N_2O_6$: Calc.: C, 64.85; H, 7.26; N, 6.03; Found: C, 64.59; H, 7.41; N, 6.29.

22. Endo-2,3-dihydro-2,2-dimethyl-N-(8-methyl-8-azabicyclo[3.2.1]oct-3-yl)-4-benzofurancarboxamide (Z)-2-butenedioate, 27% yield, m.p. 182°–184° C.

Analysis for $C_{23}H_{30}N_2O_6$: Calc.: C, 64.17; H, 7.03; N, 6.51; Found: C, 63.95; H, 6.80; N, 6.72.

23. Endo-2,3-dihydro-2,2-dimethyl-N-(8-methyl-8-azabicyclo[3.2.1]oct-3-yl)-6-benzofurancarboxamide (Z)-2-butenedioate, 43% yield, m.p. 174°–176° C.

Analysis for $C_{23}H_{30}N_2O_6$: Calc.: C, 64.17; H, 7.02; N, 6.51; Found: C, 64.11; H, 6.97; N, 6.52.

24. Endo-2,3-dihydro-2,2-dimethyl-7-benzofurancarboxylic acid, 8-methyl-8-azabicyclo[3.2.1]oct-3-yl ester (Z)-2-butenedioate, 51% yield, m.p. 174°–176° C.

Analysis for $C_{23}H_{29}NO_7$: Calc.: C, 64.02; H, 6.77; N, 3.25; Found: C, 64.02; H, 6.79; N, 3.21.

25. Endo-5-chloro-2,3-dihydro-2,2-dimethyl-7-benzofurancarboxylic acid, 8-methyl-8-azabicyclo[3.2.1]oct-3-yl ester (Z)-2-butenedioate, 48% yield, m.p. 175°–177° C.

Analysis for $C_{23}H_{28}ClNO_7$: Calc.: C, 59.29; H, 6.06; N, 3.01; Found: C, 59.19; H, 6.15; N, 2.93.

26. Exo-2,2-dimethyl-5-chloro-2,3-dihydro-7-benzofurancarboxylic acid, 8-methyl-8-azabicyclo[3.2.1]-oct-3-yl ester (Z)-2-butenedioate, 86% yield, m.p. 222°–224° C.

Analysis for $C_{23}H_{28}ClNO_7$: Calc.: C, 59.29; H, 6.06; N, 3.01; Found: C, 59.42; H, 5.88; N, 2.81.

27. dl-endo-2,3-dihydro-5-methoxy-2-methyl-N-(8-methyl-8-azabicyclo[3.2.1]oct-3-yl)-7-benzofurancarboxamide (Z)-2-butenedioate, 62% yield, m.p. 172°–174° C.

Analysis for $C_{23}H_{30}N_2O_7$: Calc.: C, 61.87; H, 6.77; N, 6.27; Found: C, 61.62; H, 6.81; N, 6.10.

28. dl-endo-2-methyl-5-methoxy-2,3-dihydro-7-benzofurancarboxylic acid, 8-methyl-8-azabicyclo[3.2.1]-oct-3-yl ester (Z)-2-butenedioate, 22% yield, m.p. 162°–164° C.

Analysis for $C_{23}H_{29}NO_8$: Calc.: C, 61.73; H, 6.53; N, 3.13; Found: C, 61.45; H, 6.68; N, 3.35.

29. Endo-2,2-dimethyl-7-chloro-2,3-dihydro-5-benzofurancarboxylic acid, 8-methyl-8-azabicyclo[3.2.1]-oct-3-yl ester (Z)-2-butenedioate, 20% yield, m.p. 154°–156° C.

Analysis for $C_{23}H_{28}ClNO_7$: Calc.: C, 59.29; H, 6.06; N, 3.01; Found: C, 59.06; H, 6.31; N, 2.95.

30. Exo-2,2-dimethyl-5-chloro-2,3-dihydro-N-( 8-methyl-8-azabicyclo[3.2.1]oct-3-yl)-7-benzofurancarboxamide (Z)-2-butenedioate, 63% yield, m.p. 129°–120.5° C.

Analysis for $C_{23}H_{29}ClN_2O_6$: Calc.: C, 58.28; H, 6.38; N, 5.91; Found: C, 58.65; H, 6.62; N, 5.72.

31. dl-endo-5-fluoro-2,3-dihydro-2-methyl-7-benzofurancarboxylic acid, 8-methyl-8-azabicyclo[3.2.1]-oct-3-yl ester (Z)-2-butenedioate, 24% yield, m.p. 154°–156° C.

Analysis for $C_{22}H_{26}FNO_7$: Calc.: C, 60.68; H, 6.02; N, 3.22; Found: C, 60.94; H, 6.21; N, 3.30.

32. dl-endo-5-chloro-2,3-dihydro-2-methyl-N-( 8-methyl-8-azabicyclo[3.2.1]oct-3-yl)-7-benzofurancarboxamide (Z)-2-butenedioate, 31% yield, m.p. 196°–198° C.

Analysis for $C_{22}H_{27}ClN_2O_6$: Calc.: C, 58.60; H, 6.04; N, 6.21; Found: C, 58.88; H, 6.26; N, 6.17.

33. dl-endo-2,3-dihydro-2-methyl-N-(8-methyl-8-azabicyclo[3.2.1]oct-3-yl)-7-benzofurancarboxamide (Z)-2-butenedioate, 43% yield, m.p. 144°–146° C.

Analysis for $C_{22}H_{28}N_2O_6$: Calc.: C, 63.45; H, 6.78; N, 6.73; Found: C, 63.72; H, 7.00; N, 6.75.

34. dl-endo-5-chloro-2,3-dihydro-2-methyl-7-benzofurancarboxylic acid, 8-methyl-8-azabicyclo[3.2.1]oct- 3-yl ester (Z)-2-butenedioate, 18% yield, m.p. 170°–172° C.

Analysis for $C_{22}H_{26}ClNO_7$: Calc.: C, 58.47; H, 5.80; N, 3.10; Found: C, 58.93; H, 6.02; N, 3.28.

35. dl-endo-2,3-dihydro-2-methyl-7-benzofurancarboxylic acid, 8-methyl-8-azabicyclo[3.2.1]oct-3-yl ester (Z)-2-butenedioate, 36% yield, m.p. 178°–179° C.

Analysis for $C_{22}H_{27}NO_7$: Calc.: C, 63.30; H, 6.52; N, 3.36; Found: C, 63.40; H, 6.76; N, 3.60.

36. Endo-2,2-dimethyl-N-(8-methyl-8-azabicyclo[3.2.1]oct-3-yl)-8-chromancarboxamide (Z)-2-butenedioate, 39% yield, m.p. 172°–174° C.

Analysis for $C_{24}H_{32}N_2O_6$: Calc.: C, 64.85; H, 7.26; N, 6.30; Found: C, 64.62; H, 7.24; N, 6.22.

37. Endo-2,3-dihydro-2,2,5-trimethyl-7-benzofurancarboxylic acid, 8-methyl-8-azabicyclo[3.2.1]oct-3-yl ester (Z)-2-butenedioate, 36% yield, m.p. 167°–168° C.

Analysis for $C_{24}H_{31}NO_7$: Calc.: C, 64.70; H, 7.01; N, 3.14; Found: C, 64.46; H, 6.74; N, 2.95.

38. dl-exo-2,3-dihydro-2-methyl-N-(8-methyl- 8-azabicyclo[3.2.1]oct-3-yl)-7-benzofurancarboxamide (Z)-2-butenedioate, 48% yield, m.p. 134°–135° C.

Analysis for $C_{22}H_{28}N_2O_6$: Calc.: C, 63.45; H, 6.78; N, 6.73; Found: C, 63.15; H, 6.53; N, 6.47.

39. Exo-2,3-dihydro-2,2-dimethyl-N-(8-methyl- 8-azabicyclo[3.2.1]oct-3-yl)-7-benzofurancarboxamide (Z)-2-butenedioate, 42% yield, m.p. 171°–173° C.

Analysis for $C_{23}H_{30}N_2O_6$: Calc.: C, 64.17; H, 7.02; N, 6.51; Found: C, 64.49; H, 7.10; N, 6.69.

40. dl-endo-2,3-dihydro-2,5-dimethyl-7-benzofurancarboxylic acid, 8-methyl-8-azabicyclo[3.2.1]oct-3-yl ester (Z)-2-butenedioate, 6% yield, m.p. 161°–164° C.

Analysis for $C_{23}H_{29}NO_7$: Calc.: C, 64.02; H, 6.77; N, 3.28; Found: C, 64.24; H, 6.54; N, 3.52.

41. Endo-2,3-dihydro-2,2-dimethyl-5-methoxy-N-( 8-methyl-8-azabicyclo[3.2.1]oct-3-yl)-7-benzofurancarboxamide (Z)-2-butenedioate, 65% yield, m.p. 189°–190° C.

Analysis for $C_{24}H_{32}N_2O_7$: Calc.: C, 62.59; H, 7.00; N, 6.08; Found: C, 62.30; H, 7.17; N, 6.03.

42. Endo-5-fluoro-2,3-dihydro-2,2-dimethyl-N-( 8-methyl-8-azabicyclo[3.2.1]oct-3-yl)-7-benzofurancarboxamide (Z)-2-butenedioate, 50% yield, m.p. 178°–180° C.

Analysis for $C_{23}H_{29}FN_2O_6$: Calc.: C, 61.60; H, 6.52; N, 6.25; Found: C, 61.31; H, 6.77; N, 6.15.

EXAMPLES 43–46

The following intermediates were prepared in the same manner as described for Examples 2–14.

43. 2,2-Dimethyl-2,3-dihydro-6-chlorobenzofuran- 7-carboxylic acid, 58% yield, m.p. 164°–166° C.

Analysis for $C_{11}H_{11}ClO_3$: Calc.: C, 58.29; H, 4.89; Found: C, 58.15; H, 4.92.

44. 4-Amino-2,3-dihydro-2,2-dimethyl-7-benzofurancarboxylic acid, 71% yield (from the N-formyl derivative of the methyl ester), m.p. 166°–169° C.

Analysis for $C_{11}H_{13}NO_3$: Calc.: C, 63.76; H, 6.32; N, 6.76; Found: C, 63.48; H, 6.55; N, 6.85.

45. 2,2-Dimethyl-4-methoxy-2,3-dihydrobenzofuran-7-carboxylic acid, 69% yield, m.p. 174°–175° C.

Analysis for $C_{12}H_{14}O_4$: Calc.: C, 64.85; H, 6.35; Found: C, 64.77; H, 6.19.

46. 2,3-Dihydro-2,2-dimethyl-6-fluoro-7-benzofurancarboxylic acid, 74% yield, m.p. 143°–145° C.

Analysis for $C_{11}H_{11}FO_3$: Calc.: C, 62.85; H, 5.27; Found: C, 62.87; H, 5.13.

EXAMPLE 47

5-Amino-4-chloro-2,2-dimethyl-2,3-dihydro-7-benzofurancarboxylic acid

A. Preparation of 4-chloro-5-nitro-2,2-dimethyl-2,3-dihydro- 7-benzofurancarboxylic acid To a mixture of 40 ml of nitric acid and 40 ml of sulfuric acid cooled to 5° C. by means of an external ice bath were added 10 g of 4-chloro-2,2-dimethyl- 2,3-dihydro-7-benzofurancarboxylic acid over a period of 28 minutes. After stirring at 5° C. for minutes, the mixture was added to ice with stirring. The resulting solid was collected by filtration and washed with water. After air drying, the residue was crystallized twice from ethyl acetate/hexane to provide 3.5 g of the desired subtitle intermediate, m.p. 260°–262° C.

Analysis for $C_{11}H_{10}ClNO_5$: Calc.: C, 48.64; H, 3.71; N, 5.16; Found: C, 48.36; H, 3.81; N, 5.30.

B. Preparation of 5-amino-4-chloro-2,2-dimethyl-2,3-dihydro- 7-benzofurancarboxylic acid A mixture of 7.53 g of the nitro intermediate named in Example 47A above in 150 ml of ethyl acetate was subjected to a hydrogen atmosphere for 16 hours in the presence of 5% palladium on carbon. The reaction mixture was filtered and the filtrate concentrated to give a residue which was crystallized from ethyl acetate/hexane providing 5.1 g of the desired title intermediate, m.p. 185°–187° C.

Analysis for $C_{11}H_{10}ClNO_3$: Calc.: C, 55.13; H, 4.21; N, 5.84; Found: C, 54.91; H, 4.50; N, 5.61.

EXAMPLE 48

5-Chloro-4-methoxy-2,2-dimethyl-2,3-dihydro-7-benzofurancarboxylic acid

A mixture of methyl 4-methoxy-2,2-dimethyl- 2,3-dihydro-7-benzofurancarboxylate, 7.1 g of pyridine, and 400 ml of tetrahydrofuran was cooled to −30° C. by means of an external dry ice/acetone bath. A solution of 27.5 g of iodobenzene dichloride in 100 ml of dry tetrahydrofuran was added dropwise to the mixture. After addition was complete, the reaction was stirred at room temperature overnight. The reaction mixture was concentrated in vacuo, water was added, and the mixture was steam distilled. To the residue were added ethyl acetate and diethyl ether. The organic mixture was washed with water, dried over sodium sulfate, and concentrated in vacuo. Eleven grams of this product were treated with 15 g of sodium hydroxide and 200 ml of water following the procedure of Example 1G above to provide 7.6 g of the desired title intermediate, m.p. 165°–166.5° C.

Analysis for $C_{12}H_{13}ClO_4$: Calc.: C, 56.15; H, 5.11; Found: C, 56.04; H, 5.21.

Following the same procedure, 19.9 g of methyl 4-amino-2,2-dimethyl-2,3-dihydro-7-benzofurancarboxylate was transformed into 20.1 g of 4-amino-5-chloro- 2,2-dimethyl-2,3-dihydro-7-benzofurancarboxylic acid, m.p. 176°–178° C.

Analysis for $C_{11}H_{12}ClNO_3$: Calc.: C, 54.67; H, 5.01; N, 5.80; Found: C, 54.43; H, 5.22; N, 5.74.

EXAMPLES 49–58

The following compounds were prepared from the corresponding carboxylic acid and the appropriate amine via the acid chloride prepared from the thionyl chloride according to the procedure of Example 16 or as generated upon treatment with phosphorous trichloride.

49. 2,3-Dihydro-5-chloro-2,2-dimethyl-N-(1-azabicyclo [2.2.2]oct-3-yl)-7-benzofurancarboxamide (Z)-2-butenedioate, 75% yield, m.p. 195°–197° C.

Analysis for $C_{22}H_{27}ClN_2O_6$: Calc.: C, 58.60; H, 6.04; N, 6.21; Found: C, 58.46; H, 6.01; N, 6.20.

50. Endo-2,2-dimethyl-2,3-dihydro-6-chloro-N-( 8-methyl-8-azabicyclo[3.2.1]oct-3-yl)-7-benzofurancarboxamide (Z)-2-butenedioate, 70% yield, m.p. 198.5°–200° C.

Analysis for $C_{23}H_{29}ClN_2O_6$: Calc.: C, 59.42; H, 6.29; N, 6.03; Found: C, 59.16; H, 6.24; N, 5.96.

51. Endo-7-chloro-2,3-dihydro-2,2-dimethyl-N-( 8-methyl-8-azabicyclo[3.2.1]oct-3-yl)-5-benzofurancarboxamide (Z)-2-butenedioate, 79% yield, m.p. 194°–196° C.

Analysis for $C_{22}H_{29}ClN_2O_6$: Calc.: C, 59.42; H, 6.29; N, 6.03; Found: C, 59.48; H, 6.23; N, 6.00.

52. Endo-2,3-dihydro-4-methoxy-2,2-dimethyl-N-( 8-methyl-8-azabicyclo[3.2.1]oct-3-yl)-7-benzofurancarboxamide (Z)-2-butenedioate, 50% yield, m.p. 194°–195° C.

Analysis for $C_{24}H_{32}N_2O_7$: Calc.: C, 62.59; H, 7.00; N, 6.08; Found: C, 62.80 ; H, 7.11; N, 6.09.

53. N-(1-azabicyclo[2.2.2]oct-3-yl)-3,4-dihydro- 2,2-dimethyl-2H-1-benzopyran-8-carboxamide (Z)-2-butenedioate, 36% yield, m.p. 169°–170° C.

Analysis $C_{22}H_{30}N_2O_6$: Calc.: C, 64.17; H, 7.02; N, 6.51; Found: C, 64.00; H, 7.03; N, 6.46.

54. Endo-5-chloro-2,3-dihydro-2,2-dimethyl-N-( 9-methyl-9-azabicyclo[3.3.1]non-3-yl)-7-benzofurancarboxamide (Z)-2-butenedioate, 20% yield, m.p. 175°–177° C.

Analysis for $C_{24}H_{31}ClN_2O_6$: Calc.: C, 60.18; H, 6.52; N, 5.84; Found: C, 60.42; H, 6.75; N, 6.03.

55. Endo-2,3-dihydro-2,2-dimethyl-N-(9-methyl-9-azabicyclo[3.3.1]non-3-yl)-7-benzofurancarboxamide (Z)- 2-butenedioate, 36% yield, m.p. 153°–154° C.

Analysis for $C_{24}H_{32}N_2O_6$: Calc.: C, 65.48; H, 7.47; N, 6.11; Found: C, 65.25; H, 7.24; N, 6.01.

56. Endo-2,3-dihydro-4-amino-5-chloro-2,2-dimethyl-N-( 8-methyl-8-azabicyclo[3.2.1]oct-3-yl)-7-benzofurancarboxamide (Z)-2-butenedioate, 45% yield, m.p. 211°–213° C.

Analysis for $C_{23}H_{30}ClN_3O_6$: Calc.: C, 57.56; H, 6.30; N, 8.76; Found: C, 57.42; H, 6.28; N, 8.63.

57. Endo-5-chloro-2,3-dihydro-4-methoxy-2,2-dimethyl-N-( 8-methyl-8-azabicyclo[3.2.1]oct-3-yl)-7-benzofurancarboxamide (Z)-2-butenedioate, 49% yield, m.p. 179°–180° C.

Analysis for $C_{24}H_{31}ClN_2O_7$: Calc.: C, 58.24; H, 6.31; N, 5.66; Found: C, 57.96; H, 6.48; N, 5.78.

58. 5-Fluoro-2,3-dihydro-2,2-dimethyl-N-(8-methyl-8-azabicyclo[3.2.1]oct-3-yl)-7-benzofurancarboxamide (Z)-2-butenedioate, 50% yield, m.p. 178°–180° C.

Analysis for $C_{23}H_{29}FN_2O_6$: Calc.: C, 61.60; H, 6.52; N, 6.25; Found: C, 61.31; H, 6.77; N, 6.15.

EXAMPLE 59

Endo-5-[(dimethylamino)sulfonyl]-2,3-dihydro-2,2-dimethyl-N-( 8-methyl-8-azabicyclo[3.2.1]oct-3-yl)-7-benzofurancarboxamide (Z)-2-butenedioate A. Preparation of 5-[(dimethylamino)sulfonyl]-2,3-dihydro- 2,2-dimethyl-7-benzofurancarboxylic acid Fifty-eight grams of chlorosulfonic acid was cooled to 10° C. and a solution of 19.2 g of 2,2-dimethyl- 2,3-dihydro-7-benzofurancarboxylic acid in 300 ml of methylene chloride was added slowly keeping the temperature between 10°–15° C. When the addition was complete, the mixture was stirred in the ice bath for two hours. The mixture was added to ice water and the resulting white precipitate recovered by filtration. The solid was added to approximately 200 ml of 40% dimethylamine in water which had been cooled to 10° C. After stirring overnight, the mixture was acidified with 6N hydrochloric acid. The resulting white precipitate was recovered by filtration. The residue was crystallized from ethyl acetate/hexane to provide 5.7 g of the desired subtitle intermediate, m.p. 211°–212° C.

Analysis for $C_{13}H_{17}NSO_5$: Calc.: C, 52.16; H, 5.72; N, 4.68; Found: C, 52.44; H, 5.79; N, 4.64.

B. Preparation of endo-5-[(dimethylamino)sulfonyl]-2,3-dihydro- 2,2-dimethyl-N-(8-methyl-8-azabicyclo[3.2.1]oct-3-yl)- 7-benzofurancarboxamide (Z)-2-butenedioate The 5.7 g of the benzofurancarboxylic acid of Example 59A above was transformed into the acid chloride and reacted with tropamine according to the procedure of Example 16 to provide 7.0 g of the desired title product, m.p. 202°–203° C.

Analysis for $C_{25}H_{35}N_3SO_8$: Calc.: C, 55.85; H, 6.56; N, 7.82; Found: C, 55.93; H, 6.56; N, 7.65.

EXAMPLE 60

2,3-Dihydro-2,2-dimethyl-N-(1-azabicyclo[2.2.2]oct-3-yl)-7-benzofurancarboxamide (Z)-2-butenedioate A mixture of 2.4 g of 2,3-dihydro-5-chloro- 2,2-dimethyl-N-(1-azabicyclo[2.2.2]oct-3-yl)-7-benzofurancarboxamide, 0.51 g of triethylamine, 0.3 g of 5% palladium on carbon, and 100 ml of ethanol were hydrogenated at 60 psi and 40°–50° C. overnight. The mixture was cooled, filtered, concentrated in vacuo, and converted into the maleate salt. Crystallization from ethanol/diethyl ether provided 2.0 g of desired title product, m.p. 182°–185° C.

Analysis for $C_{22}H_{28}N_2O_6$: Calc.: C, 63.45; H, 6.78; N, 6.73; Found: C, 63.58; H, 6.91; N, 6.86.

EXAMPLE 61

Endo-2,2-dimethyl-6-chloro-N-(8-methyl-8-azabicyclo[3.2.1]oct-3-yl)-8-chromancarboxamide (Z)-2-butenedioate Following the general procedure of Example 48, 1.96 of endo-2,2-dimethyl-N-(8-methyl-8-azabicyclo[3.2.1]oct-3-yl)-8-chromancarboxamide (Z)-butenedioate 50 ml of chloroform, 1.02 ml of pyridine, and 1.24 g of iodobenzene dichloride were allowed to react. After workup and crystallization from ethanol/diethyl acetate, 350 mg of the desired title product were isolated, m.p. 210°–211° C.

Analysis for $C_{24}H_{31}ClN_2O_6$: Calc.: C, 60.18; H, 6.52; N, 5.85; Found: C, 59.94; H, 6.47; N, 5.75.

EXAMPLE 62

Endo-2,3-dihydro-5-hydroxy-2,2-dimethyl-N-(8-methyl-8-azabicyclo[3.2.1]oct-3-yl)-7-benzofurancarboxamide (Z)-2-butenedioate A mixture of 1.4 g of endo-2,3-dihydro-5-methoxy- 2,2-dimethyl-N-(8-methyl-8-azabicyclo[3.2.1]oct- 3-yl)-7-benzofurancarboxamide and 11.5 g of pyridine hydrochloride was heated under a nitrogen atmosphere at 180° C. for three hours. The molten mixture was poured hot over ice and stirred overnight. The solution was made basic with sodium hydroxide, extracted with ethyl acetate, and carbon dioxide gas was bubbled into the basic solution to adjust the pH. Extraction with ethyl acetate and concentration of the organic solution provided a residue which was converted into the maleate salt. After crystallization from ethanol/diethyl ether, the title product (114 mg) was isolated, m.p. 228°–231° C.

Analysis for $C_{23}H_{30}N_2O_7$: Calc.: C, 61.87; H, 6.77; N, 6.27; Found: C, 61.67; H, 7.00; N, 6.21.

EXAMPLE 63

The following benzyl derivatives were prepared from the corresponding acid chloride and the appropriate 8-benzyltropanamine derivative. These compounds are useful as intermediates in that they may be deblocked (see Example 64 which follows) and alkylated with the appropriate alkylating agent to prepare the compounds of this invention. (See Example 65).

Endo-2,3-dihydro-2-methyl-N-(8-benzyl-8-azabicyclo[3.2.1]oct-3-yl)-7-benzofurancarboxamide (Z)-2-butenedioate, 70% yield, m.p. 183°–184° C.

Analysis for $C_{28}H_{32}N_2O_6$: Calc.: C, 68.28; H, 6.55; N, 5.69; Found: C, 67.98; H, 6.54; N, 5.39.

Endo-2,3-dihydro-2,2-dimethyl-N-(8-benzyl-8-azabicyclo[3.2.1]oct-3-yl)-7-benzofurancarboxamide (Z)-2-butenedioate, 49% yield, m.p. 186°–187° C.

Analysis for $C_{29}H_{34}N_2O_6$: Calc.: C, 68.76; H, 6.77; N, 5.53; Found: C, 68.97; H, 6.94; N, 5.63.

Endo-5-chloro-2,3-dihydro-2,2-dimethyl-N-(8-benzyl-8-azabicyclo[3.2.1]oct-3-yl)-7-benzofurancarboxamide, yield.

Analysis for $C_{25}H_{29}ClN_2O_2$: Calc.: C, 70.66; H, 6.88; N, 6.59; Found: C, 70.39; H, 7.00; N, 6.43.

Exo-2-methyl-2,3-dihydro-N-(8-benzyl-8-azabicyclo[3.2.1]oct- 3-yl)-7-benzofurancarboxamide-(Z)-2-butenedioate, 82%, m.p. 125°–127° C.

Analysis for $C_{28}H_{32}N_2O_6$: Calc.: C, 68.28; H, 6.55; N, 5.67; Found: C, 68.00; H, 6.61; N, 5.47.

Exo-2,2-dimethyl-2,3-dihydro-N-(8-benzyl-8-azabicyclo[3.2.1]oct-3-yl)-7-benzofurancarboxamide (Z)-2-butenedioate, 83% yield, m.p. 208.5°–210° C.

Analysis for $C_{29}H_{34}N_2O_6$: Calc.: C, 68.76; H, 6.77; N, 5.53; Found: C, 68.74; H, 7.03; N, 5.68.

EXAMPLE 64

Endo-5-chloro-2,3-dihydro-2,2-dimethyl-N-(8-azabicyclo[3.2.1]oct-3-yl)-7-benzofurancarboxamide (Z)-2-butenedioate A mixture of 3.4 g of 5-chloro-2,3-dihydro- 2,2-dimethyl-N-(8-benzyl-8-azabicyclo[3.2.1]oct-3-yl)- 7-benzofurancarboxamide, 2.0 g of 10% palladium on carbon, 0.7 ml of concentrated hydrochloric acid, and 200 ml of acetic acid were subjected to hydrogenation at a temperature of approximately 25°–30° C. After hydrogen uptake ceased, the reaction mixture was filtered, and the filtrate concentrated in vacuo. One gram of the residue was purified by high pressure liquid chromatography using 24% ethanol and 1% ammonium hydroxide in ethyl acetate as the eluant. The desired fractions were combined, concentrated in vacuo, and converted into the maleate salt. Recrystallization from ethanol/diethyl ether provided 623 mg of the desired title intermediate, m.p. 210°–212° C.

Analysis for $C_{22}H_{27}ClN_2O_6$: Calc.: C, 58.60; H, 6.04; N, 6.21; Found: C, 58.89; H, 6.14; N, 6.42.

EXAMPLE 65

The debenzylated intermediate of Example 64 can be converted into the desired N-alkyl derivative of this invention by treating the intermediate with the appropriate ($C_1$–$C_3$) alkyl iodide in tetrahydrofuran or isopropyl alcohol in the presence of sodium carbonate.

EXAMPLE 66

5-Bromo-2,3-dihydro-2,2-dimethylbenzofuran-7-carboxylic acid

The title intermediate was prepared in 20% yield from 2-methyl-2-propenyl 5-bromo-3-(2-methyl-2-propenyl)-2-hydroxybenzoate upon heating at reflux with 90% formic acid.

Analysis for $C_{11}H_{11}BrO_3$: Calc.: C, 48.73; H, 4.09; Found: C, 48.73; H, 4.13.

EXAMPLES 67–69

The following compounds were prepared from the corresponding benzofurancarboxylic acids and the appropriate amine following the procedure of Example 16.

67. Endo-5-bromo-2,2-dimethyl-2,3-dihydro-N-( 8-methyl-8-azabicyclo[3.2.1]oct-3-yl)-7-benzofurancarboxamide (Z)-2-butenedioate, 16% yield, m.p. 185°–187° C.

Analysis for $C_{23}H_{29}BrN_2O_6$: Calc.: C, 54.23; H, 5.74; N, 5.50; Found: C, 54.22; H, 5.79; N, 5.47.

68. 2,2-Dimethyl-2,3-dihydro-5-fluoro-N-(1-azabicyclo[2.2.2]oct-3-yl)-7-benzofurancarboxamide (Z)-2-butenedioate, 31% yield, m.p. 199°–200° C.

Analysis for $C_{22}H_{27}FN_2O_6$: Calc.: C, 60.82; H, 6.26; N, 6.45; Found: C, 61.07; H, 6.22; N, 6.34.

69. Endo-5-fluoro-2,3-dihydro-2,2-dimethyl-N-( 9-methyl-9-azabicyclo[3.3.1]non-3-yl)-7-benzofurancarboxamide (Z)-2-butenedioate, 16% yield, m.p. 111°–112° C.

Analysis for $C_{24}H_{31}FN_2O_6$: Calc.: C, 62.33; H, 6.76; N, 6.06; Found: C, 62.28; H, 6.70; N, 5.85.

Other compounds illustrative of this invention include:

Endo-5-methylthio-2,3-dihydro-2,2-dimethyl-N-( 8-methyl-8-azabicyclo[3.2.1]oct-3-yl)-7-benzofurancarboxamide Endo-5-methylsulfonyl-2,3-dihydro-2,2-dimethyl-N-( 8-methyl-8-azabicyclo[3.2.1]oct-3-yl)-7-benzofurancarboxamide Endo-5-methylsulfinyl-2,3-dihydro-2,2-dimethyl-N-( 8-methyl-8-azabicyclo[3.2.1]oct-3-yl)-7-benzofurancarboxamide 5-Methylthio-2,3-dihydro-2,2-dimethyl-N-(1-azabicyclo[2.2.2]oct-3-yl)-7-benzofurancarboxamide 5-Methylsulfinyl-2,3-dihydro-2,2-dimethyl-N-( 1-azabicyclo[2.2.2]oct-3-yl)-7-benzofurancarboxamide 5-Methylsulfonyl-2,3-dihydro-2,2-dimethyl-N-( 1-azabicyclo[2.2.2]oct-3-yl)-7-benzofurancarboxamide Endo-5-methylthio-2,3-dihydro-2,2-dimethyl-N-( 9-methyl-9-azabicyclo[3.3.1]non-3-yl)-7-benzofurancarboxamide Endo-5-methylsulfinyl-2,3-dihydro-2,2-dimethyl-N-( 9-methyl-9-azabicyclo[3.3.1]non-3-yl)-7-benzofurancarboxamide Endo-5-methylsulfonyl-2,3-dihydro-2,2-dimethyl-N-( 9-methyl-9-azabicyclo[3.3.1]non-3-yl)-7-benzofurancarboxamide 6-Chloro-3,4-dihydro-2,2-diethyl-N-(1-azabicyclo[2.2.2]oct-3-yl)-2H-1-benzopyran-8-carboxamide 3,4-Dihydro-2,2-diethyl-N-(1-azabicyclo[2.2.2]-oct-3-yl)-2H-1-benzopyran-8-carboxamide Endo-6-chloro-3,4-dihydro-2,2-diethyl-N-(8-methyl-8-azabicyclo[3.2.1]oct-3-yl)-2H-1-benzopyran-8-carboxamide Endo-3,4-dihydro-2,2-diethyl-N-(8-methyl-8-azabicyclo[3.2.1]oct-3-yl)-2H-1-benzopyran-8-carboxamide Endo-6-chloro-3,4-dihydro-2,2-diethyl-N-(9-methyl-9-azabicyclo[3.3.1]non-3-yl)-2H-1-benzopyran-8-carboxamide Endo-3,4-dihydro-2,2-diethyl-N-(9-methyl-9-azabicyclo[3.3.1]non-3-yl)-2H-1-benzopyran-8-carboxamide 6-Fluoro-3,4-dihydro-2,2-dimethyl-N-(1-azabicyclo[2.2.2]oct-3-yl)-2H-1-benzopyran-8-carboxamide 6-Chloro-3,4-dihydro-2,2-dimethyl-N-(1-azabicyclo[2.2.2]oct-3-yl)-2H-1-benzopyran-8-carboxamide Endo-6-fluoro-3,4-dihydro-2,2-dimethyl-N-(9-methyl-9-azabicyclo[3.3.1]non-3-yl)-2H-1-benzopyran-8-carboxamide Endo-6-chloro-3,4-dihydro-2,2-dimethyl-N-(9-methyl-9-azabicyclo[3.3.1]non-3-yl)-2H-1-benzopyran-8-carboxamide Endo-6-fluoro-3,4-dihydro-2,2-dimethyl-N-(8-methyl-8-azabicyclo[3.2.1]oct-3-yl)-2H-1-benzopyran-8carboxamide The compounds of Formula I of this invention are long-acting, orally effective specific 5-$HT_3$ receptor antagonists, rendering them useful for the treatment of migraine. Because of this mechanism, the compounds of this invention should also be useful for treating emesis, motion sickness, ischemic bowel disease, diabetic gastric paresis, relaxation of the gastrointestinal tract for instrumentation, other gastrointestinal pain following surgery, obstetrics or as in abdominal cramps, and for treating CNS disorders such as schizophrenia and anxiety. The ability of these compounds to antagonize the effects of 5-HT was assessed by their inhibition of the Von Bezold-Jarisch reflex induced by 5-HT injected intravenously into the rat (See Paintal, *Physiol. Rev.*, 53, 159 (1973)). When administered by the intravenous route 15 minutes prior to the administration of 5-HT, the compounds of this invention were effective in inhibiting the serotonin-induced Bezold-Jarisch reflex as summarized in Table 1 below:

TABLE 1

Inhibition of Serotonin-induced Bezold-Jarisch Reflex in Rats

| Compound of | Percent Inhibition of Reflex in Rats (mq/kg I.V.) | | | |
|---|---|---|---|---|
| Example No. | 0.03 | 0.01 | 0.003 | 0.001 |
| 16 | | 0.1 | | |
| 17 | 82 | 53 | –2 | |
| 18 | | 1.2 | | |
| 19 | | | 90 | 66 |
| 20 | | 16 | | |
| 21 | | 87 | 11 | 0.3 |
| 22 | | –4 | | |
| 23 | | –8 | | |
| 24 | | 38 | 21 | |
| 25 | | 83 | 19 | 10 |
| 26 | | 2 | | |
| 27 | | 20 | | |
| 28 | | 4 | | |

TABLE 1-continued

| Inhibition of Serotonin-induced Bezold-Jarisch Reflex in Rats | | | | |
|---|---|---|---|---|
| Compound of | Percent Inhibition of Reflex in Rats (mq/kg I.V.) | | | |
| Example No. | 0.03 | 0.01 | 0.003 | 0.001 |
| 29 | | −4 | | |
| 30 | | 67 | 26 | |
| 31 | | 32 | | |
| 32 | | 80 | 80 | 58 |
| 33 | 57 | 22 | | |
| 34 | | 69 | 51 | 6 |
| 35 | | 31 | | |
| 36 | | 76 | | 4 |
| 37 | | 4 | | |
| 38 | 51 | 26 | | |
| 39 | 82 | 53 | −2 | |
| 40 | | 67 | 14 | 3 |
| 41 | | −1 | | |
| 49 | | 89 | 40 | |
| 50 | | −3 | | |
| 52 | | | −7 | |
| 53 | | | 93 | 50 |
| 54 | | 94 | 84 | |
| 55 | | | 88 | |
| 56 | | 89 | 25 | |
| 57 | | 3 | | |
| 58 | | 71 | | |
| 60 | | | 87 | 25 |
| 61 | | 91 | 30 | |
| 62 | | 54 | | |

These compounds may also be used as antiemetic agents. This use is exemplified by the compound of Example 19 which effectively blocked cisplatin-induced emesis in dogs with an i.v. $ED_{50}$ of 35.6 mcg/kg. Since $5HT_3$ receptors are prevalent in the GI tract, other potential uses include other diseases of the gastrointestinal tract, such as ischemic bowel, esophageal reflux, etc.

The compounds of Formula I of this invention may be administered by various routes including the oral, rectal, transdermal, subcutaneous, intravenous, intramuscular, or intranasal routes. The compounds are usually employed in the form of pharmaceutical compositions. Such compositions are prepared in a manner well known in the pharmaceutical art and comprise at least one active compound. Accordingly, the invention includes a pharmaceutical composition comprising as active ingredient a compound of Formula I in combination with a pharmaceutically acceptable carrier, diluent, or excipient.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions usually contain active ingredient from about 1% to about 95% by weight and are preferably formulated in a unit dosage form, each dosage containing from about 0.5 to about 500 mg, more usually 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 50 mg/kg of body weight. In the treatment of adult humans, a range of from about 0.020 to about 10 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingredients any of the pharmaceutical compounds of the invention. The examples are illustrative only and are not intended to limit the scope of the invention in any way.

EXAMPLE 70

Hard gelatin capsules are prepared using the following ingredients:

| | Quantity (mg/capsule) |
|---|---|
| Endo-5-chloro-2,3-dihydro-2,2-dimethyl-N-(8-methyl-8-azabicyclo[3.2.1]-oct-3-yl)-7-benzofurancarboxamide (Z)-2-butenedioate | 250 |
| Starch dried | 200 |
| Magnesium stearate | 10 |

The above ingredients are mixed and filled into hard gelatin capsules in 460 mg quantities.

EXAMPLE 71

A tablet formula is prepared using the ingredients below:

| | Quantity (mg/tablet) |
|---|---|
| d-Endo-5-chloro-2,3-dihydro-2-ethyl-2-methyl-7-benzofurancarboxylic acid, 8-methyl-8-azabicyclo[3.2.1]-oct-3-yl ester (Z)-2-butenedioate | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 72

An aerosol solution is prepared containing the following components:

| | Weight % |
|---|---|
| l-2,3-dihydro-2-methyl-N-(8-methyl-8-azabicyclo[3.2.1]oct-3-yl)-7-benzofurancarboxamide hydrochloride | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 73

Tablets each containing 60 mg of active ingredient are made up as follows:

| | |
|---|---|
| 4-fluoro-2,3-dihydro-2,2-diethyl-7-benzofurancarboxylic acid, 8-methyl-8-azabicyclo[3.2.1]oct-3-yl ester lactobionate | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 74

Capsules each containing 80 mg of medicament are made as follows:

| | |
|---|---|
| 2,3-dihydro-2,2,5-trimethyl-N-(8-ethyl-8-azabicyclo[3.2.1]-oct-3-yl)-7-benzofurancarboxamide (Z)-2-butenedioate | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 75

Suppositories each containing 225 mg of active ingredient are made as follows:

| | |
|---|---|
| Endo-2,3-dihydro-2,2-dimethyl-N-(8-methyl-8-azabicyclo[3.2.1]-oct-3-yl)-5-benzothiophenecarboxamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 76

Suspensions each containing 50 mg of medicament per 5 ml dose are made as follows:

| | |
|---|---|
| Endo-4-chloro-2,3-dihydro-2,2-dimethyl-N-(8-methyl-8-azabicyclo-[3.2.1]oct-3-yl)-indolecarboxamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

We claim:

1. A compound of the Formula I

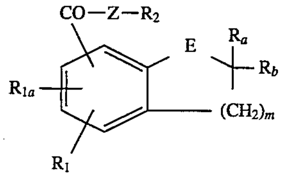

I and pharmaceutically acceptable acid addition salts thereof: wherein $R_a$ and $R_b$ are independently methyl, or ethyl, or when taken together with the carbon atom to which they are attached form a $C_3$–$C_6$ cycloalkyl ring;

E is O;

$R_1$ and $R_{1a}$ are independently hydrogen, methyl, halo, $C_1$–$C_3$ alkoxy, ($C_1$–$C_3$ alkyl)-$S(O)_t$-, trifluoromethyl, amino, hydroxy, $(CH_3)_2NSO_2$-, or ($C_1$–$C_4$ alkyl-)CONH;

m is 1;

t is 0,1, or 2;

Z is O or NH; and $R_2$ is quinuclidine, quinuclidine N-oxide, 1-azabicyclo [3.3.1]non-4-yl,

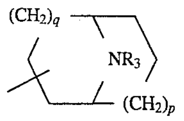

$R_2a$

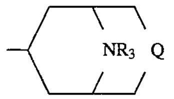

$R_2b$ or

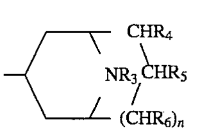

$R_2c$ wherein $R_3$ is $C_1$–$C_3$ alkyl, p and q are independently 0–2, Q is O or S; n is 0 or 1; one of $R_4$ and $R_5$ when n is 0 is $C_1$–$C_4$ alkoxy, $C_1$–$C_4$ alkoxycarbonyl, hydroxy, $C_1$–$C_4$ alkyl optionally substituted by hydroxy, $C_1$–$C_4$ alkoxy, or $C_1$–$C_4$ acyloxy and the other of $R_4$ and $R_5$ is hydrogen or $C_1$–$C_4$ alkyl; one of $R_4$, $R_5$, and $R_6$ when n is 1 is $C_1$–$C_4$ alkyl and the other two of $R_4$, $R_5$, and $R_6$ is independently hydrogen or $C_1$–$C_4$ alkyl.

2. A compound of claim 1 which is of the formula

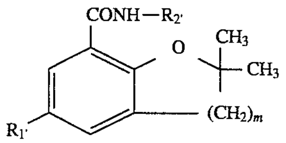

Ia wherein $R_{1'}$ is hydrogen, methyl, fluoro, bromo, or chloro, and $R_{2'}$ is endo-8-methyl-8-azabicyclo[3.2.1]oct-3-yl, 1-azabicyclo[2.2.2]oct-3-yl, or endo-9-methyl-9-azabicyclo [3.3.1]non-3-yl.

3. The compound which is endo-5-chloro- 2,3-dihydro-2,2-dimethyl-N-(8-methyl-8-azabicyclo[3.2.1]oct-3-yl)-7-benzofurancarboxamide or a pharmaceutically acceptable acid addition salt thereof.

4. The compound of claim 2 which is 2,3-dihydro-5-chloro-2,2-dimethyl-N-(1-azabicyclo[2.2.2]oct- 3-yl)-7-benzofurancarboxamide or a pharmaceutically acceptable acid addition salt thereof.

5. The compound of claim 2 which is endo- 5-chloro-2, 3-dihydro-2,2-dimethyl-N-(9-methyl-9-azabicyclo[3.3.1] non-3-yl)-7-benzofurancarboxamide or a pharmaceutically acceptable acid addition salt thereof.

6. The compound of claim 2 which is endo- 2,3-dihydro-2,2-dimethyl-N-(9-methyl-9-azabicyclo[3.3.1]non-3-yl)-7-benzofurancarboxamide or a pharmaceutically acceptable acid addition salt thereof.

7. The compound of claim 2 which is 2,3-dihydro- 2,2-dimethyl-N-(1-azabicyclo[2.2.2]oct-3-yl)- 7-benzofurancarboxamide or a pharmaceutically acceptable acid addition salt thereof.

8. A method of treating migraine, emesis, gastrointestinal disorders, schizophrenia, or anxiety in a mammal which comprises administering to said mammal an effective amount of a compound of claim 1.

9. A method of treating migraine, emesis, gastrointestinal disorders, schizophrenia, or anxiety in a mammal which comprises administering to said mammal an effective amount of a compound of claim 2.

10. A method of claim 9 employing endo- 5-chloro-2,3-dihydro-2,2-dimethyl-N-(8-methyl-8-azabicyclo[3.2.1]oct-3-yl)-7-benzofurancarboxamide or a pharmaceutically acceptable acid addition salt thereof.

11. A method of claim 9 employing 2,3-dihydro- 5-chloro-2,2-dimethyl-N-(1-azabicyclo[2.2.2]oct- 3-yl)-7-benzofurancarboxamide or a pharmaceutically acceptable acid addition salt thereof.

12. A method of claim 9 employing endo- 5-chloro-2,3-dihydro-2,2-dimethyl-N-(9-methyl-9-azabicyclo[3.3.1]non-3-yl)-7-benzofurancarboxamide or a pharmaceutically acceptable acid addition salt thereof.

13. A method of claim 9 employing endo- 2,3-dihydro-2,2-dimethyl-N-(9-methyl-9-azabicyclo[3.3.1]non-3-yl)-7-benzofurancarboxamide or a pharmaceutically acceptable acid addition salt thereof.

14. A method of claim 9 employing 2,3-dihydro- 2,2-dimethyl-N-(1-azabicyclo[2.2.2]oct-3-yl)- 7-benzofurancarboxamide or a pharmaceutically acceptable acid addition salt thereof.

15. A method of antagonizing 5-$HT_3$ receptors in a mammal which comprises administering to said mammal an effective 5-$HT_3$-antagonizing amount of a compound of claim 1.

16. A method of antagonizing 5-$HT_3$ receptors in a mammal which comprises administering to said mammal an effective 5-$HT_3$-antagonizing amount of a compound of claim 2.

17. The method of claim 16 employing endo- 5-chloro-2,3-dihydro-2,2-dimethyl-N-(8-methyl-8-azabicyclo[3.2.1] oct-3-yl)-7-benzofurancarboxamide or a pharmaceutically acceptable acid addition salt thereof.

18. The method of claim 16 employing 2,3-dihydro-5-chloro-2,2-dimethyl-N-(1-azabicyclo[2.2.2]oct- 3-yl)-7-benzofurancarboxamide or a pharmaceutically acceptable acid addition salt thereof.

19. The method of claim 16 employing endo- 5-chloro-2,3-dihydro-2,2-dimethyl-N-(9-methyl-9-azabicyclo[3.3.1] non-3-yl)-7-benzofurancarboxamide or a pharmaceutically acceptable acid addition salt thereof.

20. The method of claim 16 employing endo- 2,3-dihydro-2,2-dimethyl-N-(9-methyl-9-azabicyclo[3.3.1]non-3-yl)-7-benzofurancarboxamide or a pharmaceutically acceptable acid addition salt thereof.

21. The method of claim 16 employing 2,3-dihydro-2,2-dimethyl-N-(1-azabicyclo[2.2.2]oct-3-yl)- 7-benzofurancarboxamide or a pharmaceutically acceptable acid addition salt thereof.

22. A pharmaceutical formulation comprising a compound of claim 1 in association with a pharmaceutically acceptable carrier, diluent, or excipient.

23. A pharmaceutical formulation comprising a compound of claim 2 in association with a pharmaceutically acceptable carrier, diluent, or excipient.

24. A pharmaceutical formulation according to claim 23 wherein the compound is endo-5-chloro-2,3-dihydro- 2,2-dimethyl-N-(8-methyl-8-azabicyclo[3.2.1]oct- 3-yl)-7-benzofurancarboxamide or a pharmaceutically acceptable acid addition salt thereof.

25. A pharmaceutical formulation according to claim 23 wherein the compound is 2,3-dihydro-5-chloro- 2,2-dimethyl-N-(1-azabicyclo[2.2.2]oct-3-yl)-7-benzofurancarboxamide or a pharmaceutically acceptable acid addition salt thereof.

26. A pharmaceutical formulation according to claim 23 wherein the compound is endo-5-chloro-2,3-dihydro- 2,2-dimethyl-N-(9-methyl-9-azabicyclo[3.3.1]non- 3-yl)-7-benzofurancarboxamide or a pharmaceutically acceptable acid addition salt thereof.

27. A pharmaceutical formulation according to claim 23 wherein the compound is endo-2,3-dihydro- 2,2-dimethyl-N-(9-methyl-9-azabicyclo[3.3.1]non-3-yl)- 7-benzofurancarboxamide or a pharmaceutically acceptable acid addition salt thereof.

28. A pharmaceutical formulation according to claim 23 wherein the compound is 2,3-dihydro-2,2-dimethyl-N-( 1-azabicyclo[2.2.2]oct-3-yl)-7-benzofurancarboxamide or a pharmaceutically acceptable acid addition salt thereof.

* * * * *